(12) United States Patent
Wang et al.

(10) Patent No.: US 10,242,364 B2
(45) Date of Patent: *Mar. 26, 2019

(54) IMAGE ANALYSIS FOR USER AUTHENTICATION

(71) Applicant: Amazon Technologies, Inc., Seattle, WA (US)

(72) Inventors: Yicong Wang, Seattle, WA (US); Haizhi Xu, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/159,386

(22) Filed: Oct. 12, 2018

(65) Prior Publication Data
US 2019/0050866 A1    Feb. 14, 2019

Related U.S. Application Data

(60) Continuation of application No. 15/937,658, filed on Mar. 27, 2018, now Pat. No. 10,108,961, which is a
(Continued)

(51) Int. Cl.
*G06Q 20/40*    (2012.01)
*A61K 48/00*    (2006.01)
(Continued)

(52) U.S. Cl.
CPC ....... *G06Q 20/40145* (2013.01); *A61K 48/00* (2013.01); *G06F 21/32* (2013.01);
(Continued)

(58) Field of Classification Search
USPC .......................................... 382/100, 115, 117
See application file for complete search history.

(56) References Cited

U.S. PATENT DOCUMENTS 5,031,228 A    7/1991  Lu
5,699,449 A    12/1997 Javidi
(Continued)

FOREIGN PATENT DOCUMENTS

EP    1388802    2/2004
EP    1455297    9/2004
(Continued)

OTHER PUBLICATIONS

Rafalovitch, "Viewfinder Friends—idea for Facebook application", Nov. 14, 2007, http://blog.outerthoughts.com/2007/11/viewfinder-friends-idea-for-facebook-application/, 5 pages.
(Continued)

*Primary Examiner* — Ishrat I Sherali
(74) *Attorney, Agent, or Firm* — Davis Wright Tremaine LLP

(57) ABSTRACT

A user can be authenticated to a mobile computing device using an authentication process that recognizes the user and verifies that an actual human being is attempting to be authenticated, in order to minimize the ability of another person to spoof the authentication process. A model of a user can be generated and stored in the cloud, enabling that model to be synchronized across various devices. A user accessing one of these devices can have infrared image information captured, which can be used with a facial recognition process, to recognize the user, and with a human verification process, to verify that the facial information corresponds to a human user. Various approaches such as visual analysis and thermal imaging can be used to verify that the human user being recognized is interactive with the device.

20 Claims, 7 Drawing Sheets

Related U.S. Application Data continuation of application No. 14/887,274, filed on Oct. 19, 2015, now Pat. No. 9,934,504, which is a division of application No. 13/350,633, filed on Jan. 13, 2012, now Pat. No. 9,202,105.

(51) Int. Cl.

| | | |
|---|---|---|
| *G06F 21/32* | (2013.01) | |
| *G06K 9/00* | (2006.01) | |
| *H04N 21/44* | (2011.01) | |
| *G06Q 20/36* | (2012.01) | |
| *H04L 29/06* | (2006.01) | |
| *G06Q 30/06* | (2012.01) | |
| *G06Q 20/12* | (2012.01) | |

(52) U.S. Cl.
CPC ..... *G06K 9/00221* (2013.01); *G06K 9/00335* (2013.01); *G06K 9/00899* (2013.01); *G06K 9/00906* (2013.01); *G06Q 20/12* (2013.01); *G06Q 20/3674* (2013.01); *G06Q 20/40* (2013.01); *G06Q 20/4014* (2013.01); *G06Q 30/0643* (2013.01); *H04L 63/0861* (2013.01); *H04N 21/44008* (2013.01)

(56) References Cited

U.S. PATENT DOCUMENTS

| | | | |
|---|---|---|---|
| 5,835,616 A | 11/1998 | Lobo et al. | |
| 5,842,194 A | 11/1998 | Arbuckle | |
| 5,850,470 A | 12/1998 | Kung et al. | |
| 5,982,912 A | 11/1999 | Fukui et al. | |
| 6,134,339 A | 10/2000 | Luo | |
| 6,173,068 B1 | 1/2001 | Prokoski | |
| 6,246,779 B1 | 6/2001 | Fukui et al. | |
| 6,301,370 B1 | 10/2001 | Steffens et al. | |
| 6,310,601 B1 | 10/2001 | Moore et al. | |
| 6,389,176 B1 | 5/2002 | Hsu et al. | |
| 6,678,664 B1 | 1/2004 | Ganesan | |
| 6,687,390 B2 | 2/2004 | Avni | |
| 6,697,502 B2 | 2/2004 | Luo | |
| 6,728,401 B1 | 4/2004 | Hardeberg | |
| 6,810,149 B1 | 10/2004 | Squilla et al. | |
| 7,003,135 B2 | 2/2006 | Hsieh et al. | |
| 7,231,657 B2 | 6/2007 | Honarvar | |
| 7,333,963 B2 | 2/2008 | Widrow et al. | |
| 7,519,200 B2 | 4/2009 | Gokturk et al. | |
| 7,636,450 B1 | 12/2009 | Bourdev | |
| 7,788,247 B2 | 8/2010 | Wang et al. | |
| 7,804,982 B2 | 9/2010 | Howard et al. | |
| 7,809,722 B2 | 10/2010 | Gokturk et al. | |
| 7,945,653 B2 | 5/2011 | Zuckerberg et al. | |
| 8,121,408 B2 | 2/2012 | Omori | |
| 8,165,352 B1 | 4/2012 | Mohanty et al. | |
| 8,316,237 B1 | 11/2012 | Felsher | |
| 8,326,000 B2 | 12/2012 | Jung et al. | |
| 8,353,004 B2 | 1/2013 | Senga et al. | |
| 8,364,971 B2 * | 1/2013 | Bell | G06F 21/32 382/117 |
| 8,392,268 B2 | 3/2013 | Smith et al. | |
| 8,396,246 B2 | 3/2013 | Anbalagan et al. | |
| 8,416,312 B2 | 4/2013 | Matsunaga | |
| 8,649,604 B2 | 2/2014 | Steinberg et al. | |
| 8,750,574 B2 | 6/2014 | Ganong et al. | |
| 9,082,011 B2 * | 7/2015 | Komogortsev | A61B 5/1171 |
| 9,082,235 B2 | 7/2015 | Lau et al. | |
| 9,152,849 B2 | 10/2015 | Ganong et al. | |
| 9,202,105 B1 * | 12/2015 | Wang | G06Q 20/4014 |
| 9,600,720 B1 | 3/2017 | Gray | |
| 9,619,697 B2 | 4/2017 | Pabbichetty | |
| 9,654,469 B1 | 5/2017 | Yang | |
| 9,686,272 B2 | 6/2017 | Blinn | |
| 9,875,396 B2 * | 1/2018 | Negi | G06K 9/00899 |
| 9,934,504 B2 * | 4/2018 | Wang | G06Q 20/4014 |
| 10,108,961 B2 * | 10/2018 | Wang | G06Q 20/4014 |
| 2002/0054059 A1 | 5/2002 | Schneiderman | |
| 2002/0055955 A1 | 5/2002 | Lloyd-Jones et al. | |
| 2002/0087622 A1 | 7/2002 | Anderson | |
| 2002/0103813 A1 | 8/2002 | Frigon | |
| 2002/0191818 A1 | 12/2002 | Matsuo et al. | |
| 2003/0039380 A1 | 2/2003 | Sukegawa et al. | |
| 2003/0053663 A1 | 3/2003 | Chen et al. | |
| 2003/0063669 A1 | 4/2003 | Lee et al. | |
| 2003/0103652 A1 | 6/2003 | Lee et al. | |
| 2003/0133599 A1 | 7/2003 | Tian et al. | |
| 2003/0198368 A1 | 10/2003 | Kee | |
| 2003/0236832 A1 | 12/2003 | McIntyre et al. | |
| 2004/0070678 A1 | 4/2004 | Toyama et al. | |
| 2004/0081338 A1 | 4/2004 | Takenaka | |
| 2004/0109584 A1 | 6/2004 | Lestideau | |
| 2004/0125991 A1 | 7/2004 | Yokoi | |
| 2004/0143598 A1 | 7/2004 | Drucker et al. | |
| 2004/0190758 A1 | 9/2004 | Doi et al. | |
| 2004/0201709 A1 | 10/2004 | McIntyre et al. | |
| 2004/0264780 A1 | 12/2004 | Zhang et al. | |
| 2005/0031173 A1 | 2/2005 | Hwang | |
| 2005/0065855 A1 | 3/2005 | Geller | |
| 2005/0094849 A1 | 5/2005 | Sung et al. | |
| 2005/0100195 A1 | 5/2005 | Li | |
| 2005/0117802 A1 | 6/2005 | Yonaha et al. | |
| 2005/0141766 A1 | 6/2005 | Nagahashi et al. | |
| 2005/0180627 A1 | 8/2005 | Yang et al. | |
| 2005/0190273 A1 | 9/2005 | Toyama et al. | |
| 2005/0220347 A1 | 10/2005 | Enomoto et al. | |
| 2005/0251015 A1 | 11/2005 | Takikawa et al. | |
| 2005/0265603 A1 | 12/2005 | Porter et al. | |
| 2006/0050933 A1 | 3/2006 | Adam et al. | |
| 2006/0133672 A1 | 6/2006 | Li | |
| 2006/0173560 A1 | 8/2006 | Widrow | |
| 2006/0218225 A1 | 9/2006 | Hee Voon et al. | |
| 2006/0222215 A1 | 10/2006 | Jung et al. | |
| 2006/0239515 A1 | 10/2006 | Zhang et al. | |
| 2006/0251292 A1 | 11/2006 | Gokturk et al. | |
| 2006/0251338 A1 | 11/2006 | Gokturk et al. | |
| 2006/0251339 A1 | 11/2006 | Gokturk et al. | |
| 2006/0253491 A1 | 11/2006 | Gokturk et al. | |
| 2006/0274978 A1 | 12/2006 | Fukuda et al. | |
| 2007/0074114 A1 | 3/2007 | Adjali et al. | |
| 2007/0081744 A1 | 4/2007 | Gokturk et al. | |
| 2007/0098303 A1 | 5/2007 | Gallagher et al. | |
| 2007/0177805 A1 | 8/2007 | Gallagher | |
| 2007/0189583 A1 * | 8/2007 | Shimada | G06K 9/00255 382/118 |
| 2007/0206834 A1 | 9/2007 | Shinkai et al. | |
| 2007/0211925 A1 | 9/2007 | Aoki et al. | |
| 2008/0046458 A1 | 2/2008 | Tseng et al. | |
| 2008/0077595 A1 | 3/2008 | Leebow | |
| 2008/0080743 A1 | 4/2008 | Schneiderman et al. | |
| 2008/0080745 A1 | 4/2008 | Vanhoucke et al. | |
| 2008/0091723 A1 | 4/2008 | Zuckerberg et al. | |
| 2008/0130960 A1 | 6/2008 | Yagnik | |
| 2008/0212849 A1 | 9/2008 | Gao | |
| 2008/0317379 A1 | 12/2008 | Steinberg et al. | |
| 2009/0185784 A1 | 7/2009 | Hiroike et al. | |
| 2009/0232367 A1 | 9/2009 | Shinzald | |
| 2009/0252383 A1 | 10/2009 | Adam et al. | |
| 2009/0254448 A1 | 10/2009 | Giobbi | |
| 2009/0324018 A1 | 12/2009 | Tell | |
| 2009/0324022 A1 | 12/2009 | Sangberg et al. | |
| 2009/0324137 A1 | 12/2009 | Stallings et al. | |
| 2010/0054600 A1 | 3/2010 | Anbalagan et al. | |
| 2010/0054601 A1 | 3/2010 | Anbalagan et al. | |
| 2010/0061631 A1 | 3/2010 | Omori | |
| 2010/0232656 A1 | 9/2010 | Ryu | |
| 2010/0245614 A1 | 9/2010 | Matsunaga | |
| 2010/0272363 A1 | 10/2010 | Steinberg et al. | |
| 2010/0287053 A1 | 11/2010 | Ganong et al. | |
| 2010/0317420 A1 | 12/2010 | Hoffberg | |
| 2011/0063108 A1 | 3/2011 | Aonuma et al. | |
| 2011/0202531 A1 | 8/2011 | Zuckerberg et al. | |
| 2011/0225481 A1 | 9/2011 | Zuckerberg et al. | |
| 2013/0057693 A1 | 3/2013 | Baranek | |
| 2013/0077835 A1 | 3/2013 | Kritt et al. | |

(56) References Cited

U.S. PATENT DOCUMENTS

| | | | |
|---|---|---|---|
| 2013/0219480 A1 | 8/2013 | Bud | |
| 2013/0267204 A1 | 10/2013 | Schultz et al. | |
| 2015/0131872 A1 | 5/2015 | Ganong et al. | |
| 2016/0335511 A1 | 11/2016 | MacDonald | |
| 2017/0323167 A1* | 11/2017 | Mapen | G06K 9/4661 |

FOREIGN PATENT DOCUMENTS

| | | |
|---|---|---|
| WO | WO2006130542 | 12/2006 |
| WO | WO2008107002 | 9/2008 |
| WO | WO2015070320 | 5/2015 |

OTHER PUBLICATIONS

Kishore, "How to Add, Upload, and Tag Your Pictures and Photos in FaceBook", http://www.online-tech-tips.com/fun-stuff/how-to-add-upload-and-tag-your-pictures-and-photos-in-facebook/, Aug. 11, 2007, 13 pages.

Becker et al., "Evaluation of Face Recognition Techniques for Application to Facebook", IEEE International Conference on Automatic Face and Gesture Recognition, 2008, 6 pages.

Bletsko et al., "Using Skin-Color Motion for 3D Face Modelling and Synthesis", Sep. 6, 2003, WISP 2003, pp. 295-299.

Baker, "Google & Riya Face Recognition Photo Search", Nov. 22, 2005, http://www.searchenginejournal.com/google-riya-face-recognition-photo-search/2550/, 1 page.

Ponce, "Riya, Photo Sharing with Face Recognition", Oct. 28, 2005, http://www.ohgizmo.com/2005/10/28/riya-photo-sharing-with-face-recognition/, 2 pages.

Facebook, "Making Photo Tagging Easier", https://m.facebook.com/notes/facebook/making-photo-tagging-easier/467145887130/?_tn_=C&._rdr, 2 pages.

Michelson et al., "Auto-tagging the Facebook", 2006, http://cs229.stanford.edu/proj2006/MichelsonOrtiz-AutoTaggingTheFacebook.pdf, 5 pages.

Arrington, "First Screeen Shots of Riya", Oct. 26, 2005, http://techcrunch.com/2005/10/26hiya-prepares-to-aunch-alpha/, 10 pages.

Arrington, "Ojos—Auto Name & Tag Your Photos", Aug. 15, 2005, http://techcrunch.com/2005/08/31/ojos-auto-name-tag-your-photos/, 8 pages.

Stone, et al., "Autotagging Facebook: Social network context improves photo annotation," In Workshop on Internet Vision, 2008, 2 pages.

Schuon et al., "CS229 Project Report: Automated photo tagging in Facebook", Dec. 2007, http://cs229.stanford.edu/proj2007/SchuonRobertsonZou-AutomatedPholoTaggingInFacebook.pdf, 5 pages.

Yadav, "Facebook—The Complete Biography", Aug. 25, 2006, http://mashable.com/2006/013/25/facebook-profile/, 7 pages.

Unknown, "What does it mean to "tag" someones picture on facebook, whets the point of doing it?", Nov. 28, 2007, https://answers.yahoo.com/question/index?qid=20071128123629AAY0DLP, 2 pages.

Yang et al., "Detecting Faces in Images: A Survey", Jan. 2002, IEEE Trans. Pattern Analysis Machine Intelligence, 24(1), 2 pages.

* cited by examiner

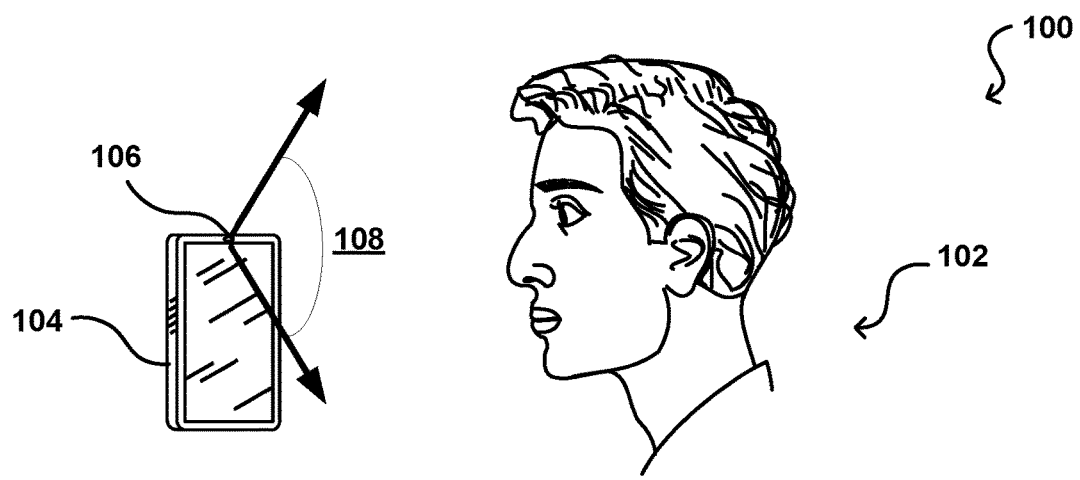
FIG. 1(a)
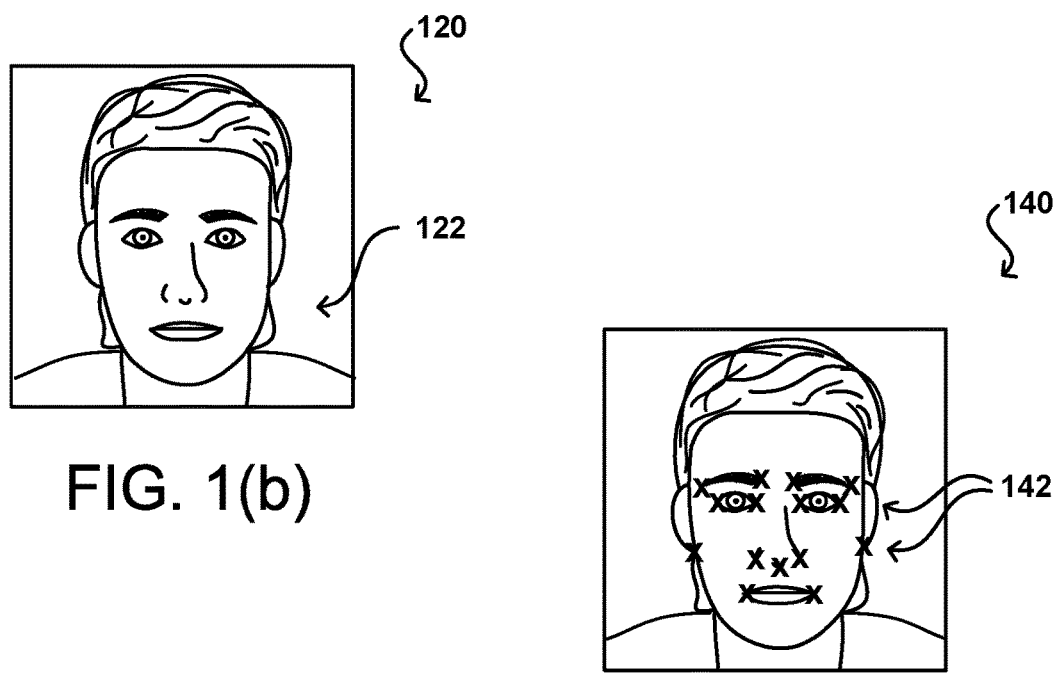
FIG. 1(b)
FIG. 1(c)

IMAGE ANALYSIS FOR USER AUTHENTICATION

CROSS-REFERENCE TO RELATED APPLICATIONS

This application is a continuation of U.S. patent application Ser. No. 15/937,658, filed Mar. 27, 2018, entitled "IMAGE ANALYSIS FOR USER AUTHENTICATION," which is a continuation of U.S. patent application Ser. No. 14/887,274, filed Oct. 19, 2015, now U.S. Pat. No. 9,934,504, entitled "IMAGE ANALYSIS FOR USER AUTHENTICATION," which is a divisional of U.S. patent application Ser. No. 13/350,633, filed Jan. 13, 2012, now U.S. Pat. No. 9,202,105, entitled "IMAGE ANALYSIS FOR USER AUTHENTICATION," the disclosures of which are hereby incorporated herein in their entirety.

BACKGROUND

As people are utilizing computing devices for an increasing variety of tasks, there is a corresponding need to improve the security available for these tasks. While many conventional approaches rely on password entry for user authentication, these passwords can be stolen or discovered by other persons who can impersonate the user for any of a variety of tasks. Further, the entry of these passwords on portable devices is not user friendly in many cases, as the small touchscreen or keyboard elements can be difficult to accurately select using a relatively large human finger, and can require the user to turn away from friends or co-workers when entering a password, which can be awkward or embarrassing in many situations. In order to avoid typing in long passwords in such situations, users often have their passwords stored on their devices or enable information to be stored elsewhere such that an activity can be performed without manually re-entering the password. When using such an approach, however, another person having access to that device can impersonate the user for any task associated with the store password. As a compromise some users utilize short and simple passwords, but these passwords can be easily hacked by an unscrupulous user or application. Certain approaches attempt to improve security by adding biometric identification. For example, a computing device might capture an image of a user and analyze that image to attempt to recognize the user using facial recognition software. Such a process provides only a certain level of additional protection, however, as the facial recognition process can often be spoofed by holding a picture of the user in front of the camera, as the resulting two-dimensional image can look substantially the same whether taken of the user or a picture of the user.

BRIEF DESCRIPTION OF THE DRAWINGS

Various embodiments in accordance with the present disclosure will be described with reference to the drawings, in which:

FIGS. 1(a), (b), and (c) illustrate an example situation wherein a computing device is configured to capture image information including a user and perform facial recognition on the captured image information in accordance with various embodiments;

DETAILED DESCRIPTION

Figure 2A:
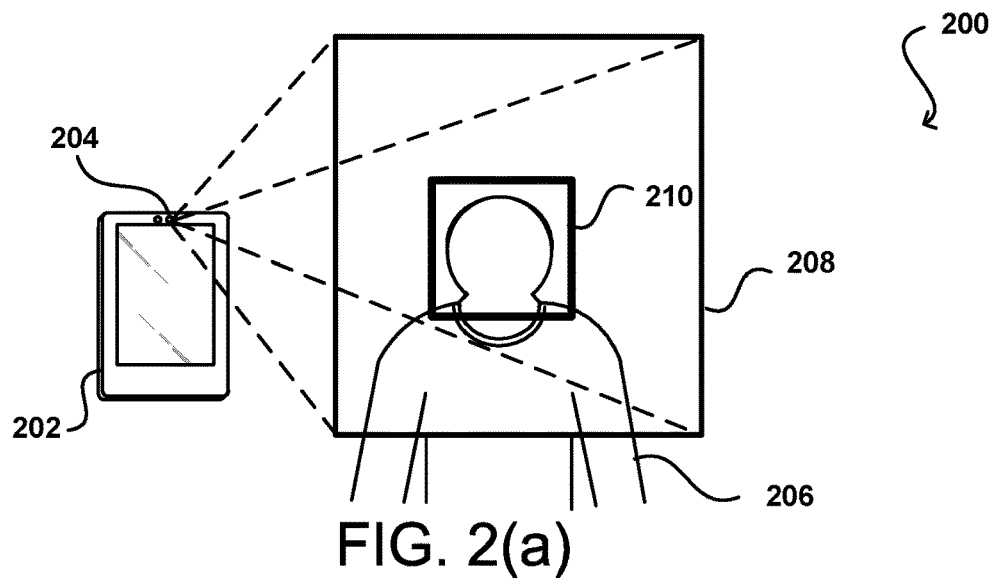
FIGS. 2(a), (b), (c), (d), and 2(e) illustrate example situations where additional information can be utilized to attempt to determine that the captured image information corresponds to a physical user in accordance with various embodiments.

Systems and methods in accordance with various embodiments of the present disclosure may overcome one or more of the aforementioned and other deficiencies experienced in conventional approaches to authenticating a user of a computing device. In particular, various embodiments utilize an image-inclusive approach to authenticating a user of a computing device, which can be implemented at an application level and/or by sharing user information across multiple devices. In at least some embodiments, a user can be verified to perform a task, access data or functionality, or otherwise interact with a computing device by enabling the computing device to capture image information about the user that can assist in authenticating the user. For example, a computing device can capture image information for use in performing facial recognition to determine an identity of the user. In order to provide a further level of authentication, the device can utilize the same, different, or additional image information to verify that the image information corresponds to a physical being and not a representation of a user, such as may be provided through a picture or video of a user.

For example, a computing device can capture video information of the user over a period of time to determine whether the user performs an action indicative of a physical person, such as by blinking or making another such motion. In some embodiments, the device can prompt the user to perform certain actions, motions, or gestures, such as to smile, blink, or tilt his or her head. The device (or a system or service in communication with the device) then can analyze the captured video to determine whether the video likely corresponds to a physical user when the prompted action is observed, and in at least some embodiments can further authenticate an identity of the user when a motion of the action matches a model of the user performing that action with at least a minimum level of confidence. The device can also capture various other types of image information as well, such as infrared image information, thermal imaging data, or other such information which can assist in determining the presence of a human user. In at least some embodiments, two or more of these approaches can be combined to improve an accuracy of the determinations.

Various other applications, processes and uses are presented below with respect to the various embodiments.

As mentioned, various computing devices can attempt to authenticate a user through a facial recognition process. FIG. 1(a) illustrates an example situation 100 wherein a camera 106 of a computing device 104 is able to capture image information regarding objects within a field of view 108 of that camera. Although a portable computing device (e.g., a smart phone, an e-book reader, or tablet computer) is shown, it should be understood that various other types of electronic devices that are capable of determining and processing input can be used in accordance with various embodiments discussed herein. These devices can include, for example, notebook computers, personal data assistants, video gaming consoles or controllers, and portable media players, among others. The computing device 104 can include one or more cameras or other such capture elements operable to perform functions such as image and/or video capture, positioned at any appropriate location on the device. Each image capture element may be, for example, a camera, a charge-coupled device (CCD), a motion detection sensor, or an infrared sensor, or can utilize another appropriate image capturing technology. In FIG. 1(a), the head of a user 102 is positioned within the field of view 108 of the camera 106, such that the computing device capture image information including at least a portion of the user's face to analyze using a facial recognition process or other such application.

FIG. 1(b) illustrates an example image 120 that could be captured of a user's face 122 in accordance with various embodiments. After any pre-processing or filtering, as known in the art for improving a quality of image capture, the image 120 can be fed to a facial recognition process, for example, that is operable to analyze the image to attempt to locate the user's face and any landmarks or features of the face that can be helpful in identifying the user. For example, FIG. 1(c) illustrates an example set 140 of landmark or feature locations 142 that can be determined using such a process. In at least some embodiments, the relative locations of these features can be compared to a library or set of facial feature locations for one or more users, in order to attempt to match the relative features locations with the stored feature locations of a user of the device. Various pattern or point matching algorithms can be used for such processes as known in the art. If the relative point distribution, or other such data set, matches the information for a user with at least a minimum level of confidence, the user can be authenticated to the device (assuming the identified user matches any information manually provided by the user, for example).

As discussed, however, such a process can potentially be spoofed by holding or otherwise providing a picture or other representation of an authorized user within a field of view of a camera of a computing device, as the relative point distribution determined from the image will be substantially the same as if the computing device was capturing an image of the actual user. For example, FIG. 1(b) would look substantially the same if the camera took a picture of the user, the picture was printed out, and that picture was then held in front of the camera for a subsequent picture (other than potential differences in lighting, coloration, etc.).

Accordingly, systems and methods in accordance with various embodiments can perform an additional image analysis step or process in order to attempt to verify that the captured image actually corresponds to a living, physical being in the field of view of a camera of a computing device. FIG. 2(a) illustrates an example situation 200 wherein a user 206 is positioned within a field of view 208 of a camera 204 of a computing device 202. In some embodiments, the camera 204 can be a video capture element capable of capturing a substantially continuous stream of image information, at least over a specified period of time. Since it can be very resource intensive to process the entire video stream using facial detection algorithms or other such processes, various approaches can instead utilize a less robust algorithm, such as a pattern matching algorithm, to attempt to identify the presence of a person's head or other such feature in the image stream. For example, in FIG. 2(a) a pattern matching algorithm can look for a contour or shape that matches the shape of a human head within a specified level or range of certainty. Upon detecting such a shape or contour, the device can track a relative position or area 210 in the captured image information corresponding to the user's head. Approaches for detecting and tracking shapes or contours are known in the art and as such will not be discussed herein in detail. In at least some embodiments, the detection of a user's head can cause at least one user authentication process to be activated.

In certain embodiments, a single image might be captured of the user for purposes such as facial recognition. In at least some embodiments, however, one or more additional images and/or video of the user can be captured to assist in determining whether the image information being captured corresponds to a physical human positioned relative to the device. In at least some embodiments, head tracking can be used to reduce the amount of image information that must be analyzed in accordance with various embodiments, in order to reduce the amount of resources needed for the processing, etc.

Figure 2B:
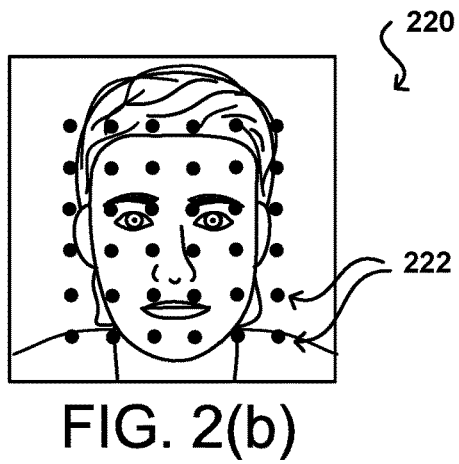

In at least one embodiment, an infrared emitter and detector can be used to determine shape information of the head being imaged in accordance with various embodiments. The infrared emitter can be any appropriate emitter, such as may include one or more infrared (IR) LEDs, and the infrared detector can be any appropriate detector, such as at least one IR sensor or a camera operable to capture light in at least the infrared spectrum. In at least some embodiments, the IR emitter can be configured to emit a pattern of infrared light, such as a regular pattern of commonly sized dots of similar intensity. Such a pattern can be advantageous, as the reflection of the pattern can provide information about the object reflecting the light. For example, FIG. 2(b) illustrates an example image 220 that can be captured by an infrared sensor, for example, that shows the reflected pattern of infrared dots 222. As illustrated in this example image, the reflected dots are still in a regular pattern with a similar intensity. Accordingly, it can reasonably be determined that the pattern is being reflected from a two-dimensional surface, such as a photograph of a user.

Various depth sensors can be used as well, such as distance sensors or other elements that can be used with the image information to generate a three-dimensional model of the face being captured. Other approaches such as stereoscopic imaging can be used as well. By generating three-dimensional mapping information, which can be relatively low resolution in at least some embodiments, a determination can be made as to whether the camera is capturing image information of a three-dimensional head or a two-dimensional photograph or video display. In a potentially less resource intensive process, the image information from stereo images can be compared without generating a three-dimensional map or set of disparity information, as the head would have a slightly different pose from each camera and the head having the same pose in images captured from both cameras would be indicative of a photograph instead of a physical user.

Figure 2C:
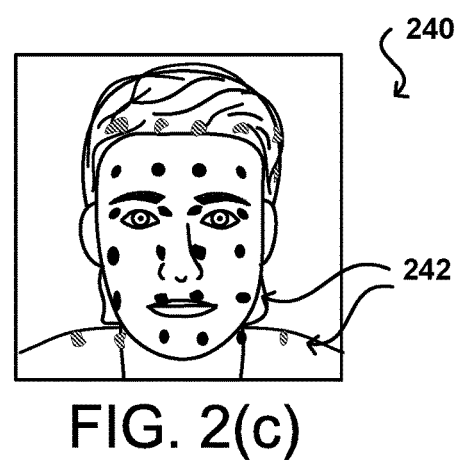

In the example image 240 of FIG. 2(c), the reflected pattern of infrared dots 242 is substantially different from the pattern that was projected from the device. For example, portions of the pattern that were not incident on the user are not shown in the reflected image. Further, the dots that are shown are of different shape, size, and intensity, indicating that the pattern is falling on, and being reflected by, a three-dimensional object. Further still, a human face has varying hardness and reflectivity values, so dots at different locations will be reflected with different intensity. In at least some embodiments, a threshold amount of variation in the pattern can be sufficient to indicate that the imaged object is not a photo or video, which can be sufficient for at least some applications. In some embodiments, the reflected pattern can be analyzed to determine whether the pattern matches a pattern that would be reflected from an object shaped like a human face, reflected with deviations that match the user's face, or other such information, in order to provide yet another level of accuracy for user authentication. Various other approaches can be used as well as should be apparent. For example, an infrared bar can be scanned across a user's face to look for variations in the shape of the bar, a spot can be moved across the face in a raster pattern to look for deviations, etc.

Figure 2D:
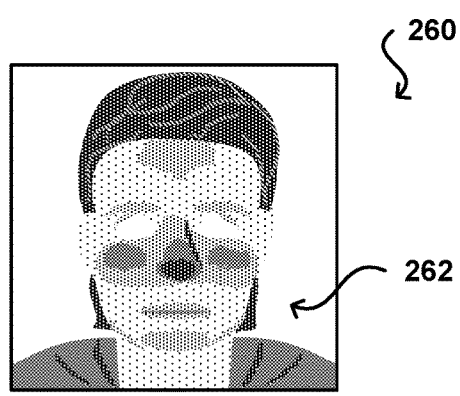

In another embodiment, a thermal imaging approach can be used to attempt to determine whether the image information corresponds to a physical being. For example, a computing device can include a thermographic camera, infrared camera, or other such sensor or component operable to capture infrared energy emitted, transmitted, or reflected by an object. FIG. 2(d) illustrates an example image 260 illustrating thermographic variations that can be captured and analyzed in accordance with various embodiments. As illustrated, there can be significant variations in the thermal readings 262 for different portions of a user's face and head. The thermal image captured of a human face will be very different than one captured for a piece of paper, as there will be a significant variance in the thermal characteristics of regions such as the eyes, nose, and mouth of a physical user, while these variations will not be present in a photograph. In some embodiments, a determination of at least a threshold amount of variation can be sufficient to determine that the object being imaged is not a picture or video, or other non-living object. In at least some embodiments, the actual pattern or amount of variation can be analyzed and compared to information stored for a human face and/or the actual user's face. Such information can be used to provide a further level of accuracy for image-based user authentication.

Figure 2E:
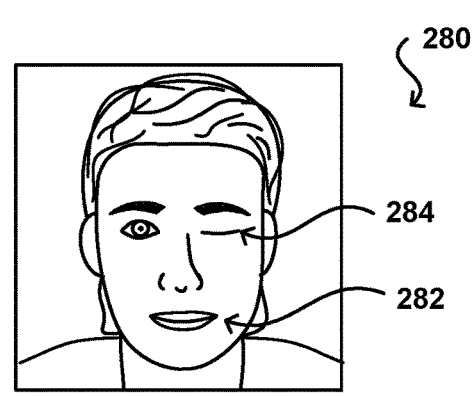

In another embodiment, a user can be asked to perform a specific motion, gesture, or action within the field of view of the camera to help verify that the image information corresponds to a physical human user. The device might select one of a plurality of different actions at random, in order to minimize the ability of someone to provide video of a user performing the specified action within a specified period of time, such as within five seconds of prompting by the device. In this example, the user has been asked to perform an action such as to blink the user's left eye 284 or smile 282, or a combination of both, as illustrated in the example image 280 of FIG. 2(e). The action can be any action that is recognizable by the device when performed by a user, such as upon analysis by at least one feature detection algorithm or pattern matching algorithm. In some embodiments, an amount of detectable motion or variation of the face in the image can be sufficient, while in other embodiments the actual motion can be analyzed to see if the action corresponds to the prompted action, and in at least some embodiments the action can be compared to information stored for the user previously performing that action, to determine whether the person performing the action is likely the user. Other motions or actions can be used as well, such as opening and closing the user's mouth, frowning, rotating the user's head, nodding, or performing another such action that cannot be replicated with a two-dimensional image (i.e., not just a tilting of the head in a plane parallel to the device).

In some embodiments, the device might not prompt a user to perform an action, at least over a specific period of time, but instead might monitor the user for natural motions or actions. For example, an average person will blink his or her eyes about once every twenty-five to thirty seconds. If a computing device captures video information for a period of sixty seconds, for example, and the video does not contain a single eye blink (e.g., an eye open for at least five seconds followed by a closure of less than a second) then the image information can be considered to include a non-human representation, instead of a live person. Other detected motions of the face can be used as well, but these motions should be motions that cannot be faked using a photograph. For example, a user holding a hand up in front of the face might not be a valid motion, as an unauthorized person could hold their hand in front of a photograph of an authorized user, etc.

In some embodiments, a computing device with at least one infrared (IR) emitter and receiver can look for objects corresponding to the human eye in the captured image information, where the IR was reflected back from one or more objects within a field of view of the IR receiver. As known in the art, the human eye reflects IR radiation differently than the rest of the human head, such that the presence and/or position of a user's eyes can quickly be detected and/or located by analyzing a captured IR image. Such information can help determine the presence of a user's head without requiring significant image processing, and can also help improve the perspective determinations in at least some embodiments.

Figure 3:
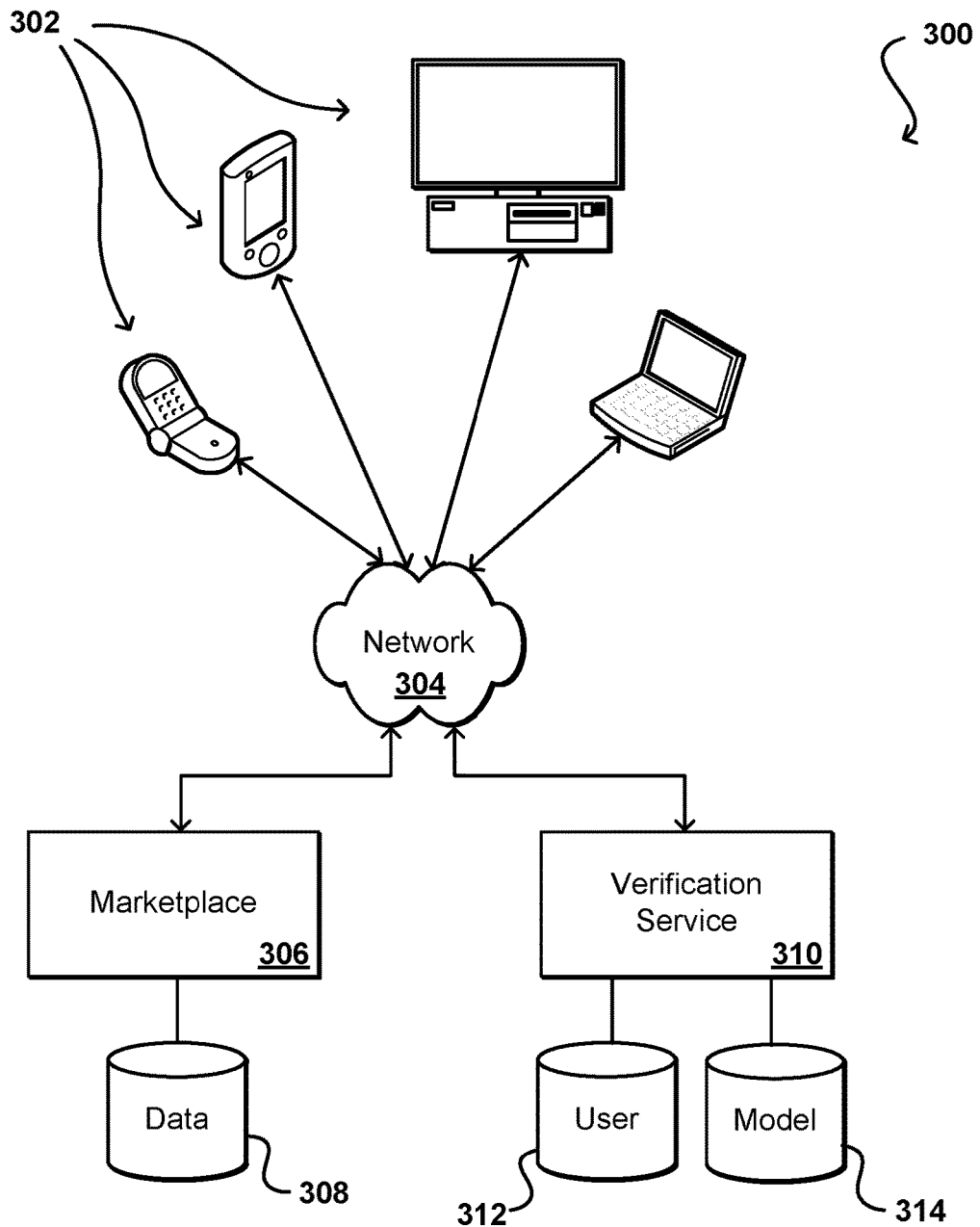
FIG. 3 illustrates an example environment in which aspects of the various embodiments can be implemented.

FIG. 3 illustrates an example environment 300 in which various aspects can be implemented in accordance with various embodiments. In this example, a user can utilize any appropriate computing device 302 to attempt to access content and/or functionality on the device. The content can include content stored on the device, such as a game or application stored locally, or can come from across at least one network 304, such as pages of an electronic marketplace 306 provided by an electronic retailer or other such entity. It should be understood that while an electronic marketplace is used as an example, any appropriate type of content can be accessed within the scope of the various embodiments, as may include financial information, personal records, news content, gaming content, and the like. Further, an authentication process might be used on the device to allow any such access, after which a user has access to any of a number of different types of content from any of a number of different sources.

In this example, the user submits a request across at least one network 304, such as an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections, and combinations thereof. The request can be received to the electronic marketplace system 306, which can locate content such as information about products offered for consumption (e.g., purchase, rent, borrow, lease, or download), as may be located in at least one data store 308 for the marketplace, and provide that content for display on the client computing device 302 from which the request was initiated.

During a user session with the electronic marketplace, a user might want to perform an action such as to access user account information or purchase an item. Such actions might require the user to be authenticated to the electronic marketplace. While in some embodiments a password or similar authentication mechanism can be used, in this example the computing device 302 being operated by the user can be triggered to capture image information about the user. In some embodiments, the computing device or electronic marketplace might first contact an entity such as a verification service 310 in order to initiate a verification session and/or determine a type of image information to be captured. In other embodiments, an application executing on the computing device can cause image information to be captured of a user, which can be analyzed on the device and/or uploaded to the verification service 310 for analysis. In at least some embodiments, a decision as to whether to process information on the user device or using an external service or network device can be based on any of a number of factors, such as a current level of network bandwidth, network availability, cost of sending the data, power consumption of the local computation, remaining battery power of the device, and processing latency, among other such factors. The decision also can be made using logic on the device, at the electronic marketplace, or any other appropriate location. In at least some embodiments, an amount of pre-processing can be performed on the device, after which at least portions of the processed image information can be uploaded for further processing. In this example, the verification service 310 receives image information that can be compared against information stored for the purported user, such as in a user data store 312, in order to determine whether the person operating the device matches the purported user. As part of the analysis, the verification service can perform facial recognition on the uploaded image information. As another part of the analysis, the verification service 310 can also analyze the image information to attempt to determine whether the image information corresponds to an actual human. In some embodiments the same image information is analyzed as for the facial recognition process, while in other embodiments other image information can be used, as may be captured at different times, under different conditions, and/or captured using a different camera or sensor.

The verification service 310 (or a user device, etc.) can use any approach or combination of approaches discussed or suggested herein to attempt to authenticate the user. In some embodiments, the service might pull information from a model data store 314 or other such location, which can store user models, feature models, processing algorithms, and the like, in order to analyze the uploaded image information. If additional image information is needed, such as where the verification service cannot make a determination with a minimum level of confidence, the verification service can send a request to the computing device to capture additional image information, prompt the user to perform, and action, etc. Once the analysis has been completed, whether on the device or through the verification service, the result can be provided to the computing device 302 and/or the electronic marketplace 306, whereby the action desired to be performed by the user can be allowed or disallowed based at least in part upon whether the user was authenticated. Various other approaches can be used as well as discussed and suggested elsewhere herein.

Figure 4A:
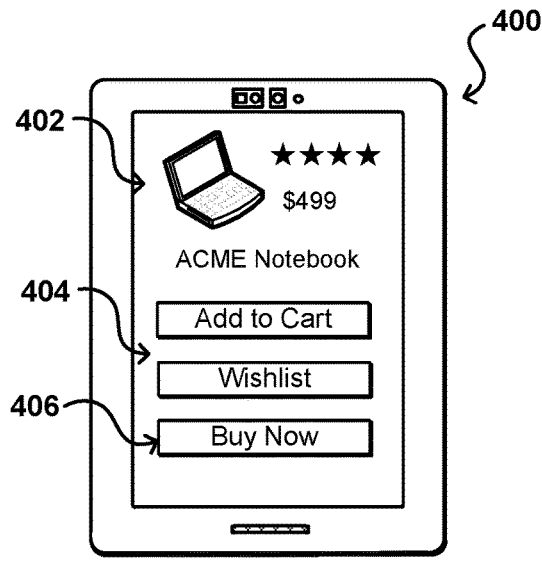
FIGS. 4(a), (b), (c), and (d) illustrate example interface displays that can be provided on a computing device as part of a checkout process in accordance with various embodiments.
Figure 4B:
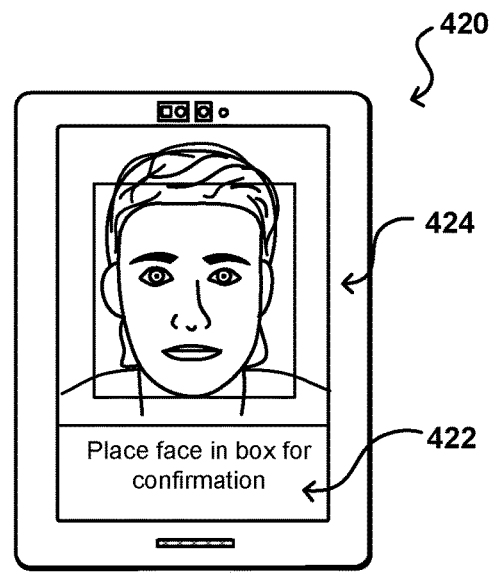
Figure 4C:
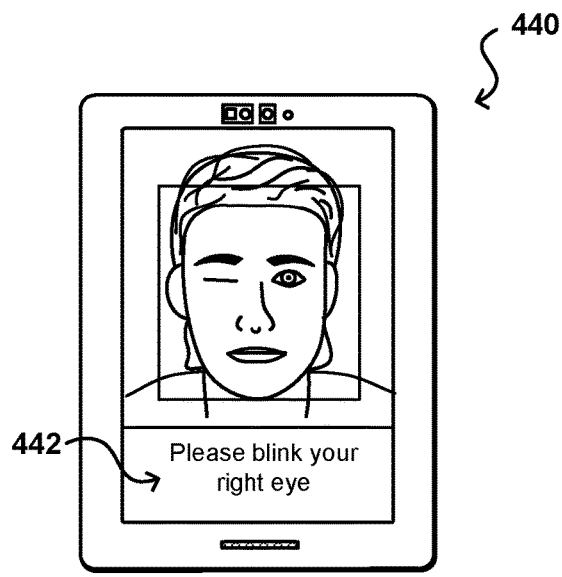
Figure 4D:
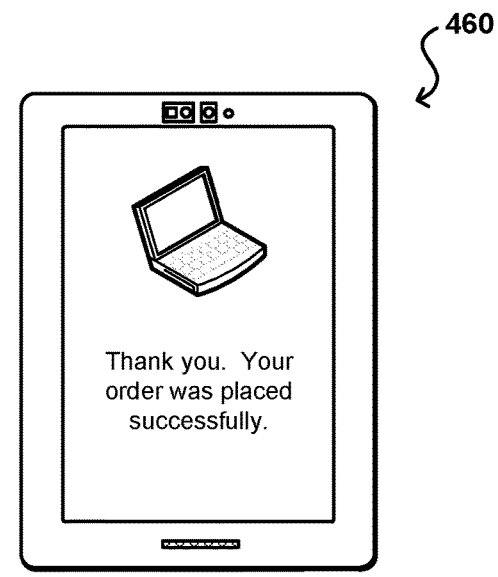

FIGS. 4(a)-(d) illustrate states of an example interface that can be displayed to a user as part of the authentication process in accordance with various embodiments. For example, FIG. 4(a) illustrates a state 400 where a user is browsing content for a notebook computer 402 offered through an electronic marketplace. If the user is interested in the notebook, the user can select options 404 relating to the notebook, such as to add the notebook to a virtual shopping cart or a wishlist for the user. In this example, the user also has an option 406 to buy the item using an identity verification process or other such approach. In this example, selecting the option to purchase through user authentication can cause an interface state 420 to appear that provide instructions 422 to the user to perform an initial action with respect to the device. In this example, the interface asks the user to place his or her face in a particular position with respect to the device such that the face is within a box 424 or region of analysis as illustrated in FIG. 4(b). When the user's face is in the proper location, the face can be detected by the device and image information analyzed using a facial recognition or other such process, either on or remote to the device. As another portion of the authentication process, the interface in this example can enter another state 440 where information 442 is provided to the user instructing the user to perform a particular action, such as is illustrated in FIG. 4(c). For a period of time after the instructions are initially provided, video information can be captured which then can be analyzed to determine whether the user performed the requested action within a determined period of time. If not, the user may not be authenticated, or may have to go through another step to be authenticated. If the user is recognized and has performed the requested action, the user can be authenticated to the device, and the transaction can be completed without further action or input from the user. Accordingly, an interface state 460 such as that illustrated in FIG. 4(d) can be displayed that indicates to the user that the notebook was successfully purchased. As mentioned previously, it should be understood that an e-commerce setting is merely an example, and that such an approach can be used to enable a user to view financial information, stream music, access a save file for a video game, or otherwise access data or functionality within the scope of the various embodiments.

Such approaches provide for user authentication without the user having to physically interact with a computing device, which can enable a user to access information by looking at a camera, performing a simple gesture such as a smile, or performing another such action. Such an authentication can be user friendly, particularly with respect to conventional approaches such as typing and remembering long passwords, and can provide enhanced security because it can be difficult for another person to replicate a user's face in three dimensions. A user can provide authentication while in public without people nearby being able to tell, and even a person discovering a password or stealing the user's device will not be able to access the information protected by image-based security approaches discussed herein. Such an approach also can improve the user experience, as a smile or wink-based approach can be fun for some users. Such approaches can utilize still image or video information, as may be based at least in part upon the capabilities of the device, the amount of remaining battery power, or other such aspects. Further, certain embodiments enable a user to set up the authentication information or service once and then access that information from various devices for various purposes and applications. As mentioned, a Web service or other such entity can manage the authentication process and make the authentication information available from any appropriate location. Such approaches can also create a new data point for business intelligence and fraud detection.

As mentioned, an authentication process in accordance with various embodiments can include at least two phases: a configuration phase and an execution phase. The configuration phase can run once per user in order to obtain the necessary information, after which time the information can be available from any appropriate device in the execution phase. In at least some embodiments, however, the user can have the option or re-running the configuration phase, or the configuration can update over time as the user grows, the recognition information changes slightly, etc. In the configuration phase, a user can select configuration settings based on factors such as need and preference. The configuration phase can collect information such as the identity of the user, as well as image information useful in authenticating the user. For example, an authentication module might take photos and video clips of the user to analyze and/or use in building models of the user. Information about a user's face or other such features then can be stored by the device and/or uploaded to a location such as a cloud provider for use in subsequent authentication. When the user subsequently performs an action during the execution phase, such as by selecting an option that requires authentication, an authentication module executing on the device can invoke a front-facing camera of the computing device to capture photos or a video clip of the person using the physical device. The authentication module can attempt to recognize the face of the person as an authorized user, such as the user currently logged into an application. The authentication module can also attempt to determine that the image information corresponds to a physical person. Once the face is recognized, and this "hidden" human identification process provides approval, the requested action can proceed. If the face cannot be recognized, or the image cannot be determined to correspond to an actual human, the checkout can be blocked and further security actions activated, as may include notifying the customer by email, providing a mobile notification or phone call, and/or prompting for email password authentication.

Figure 5:
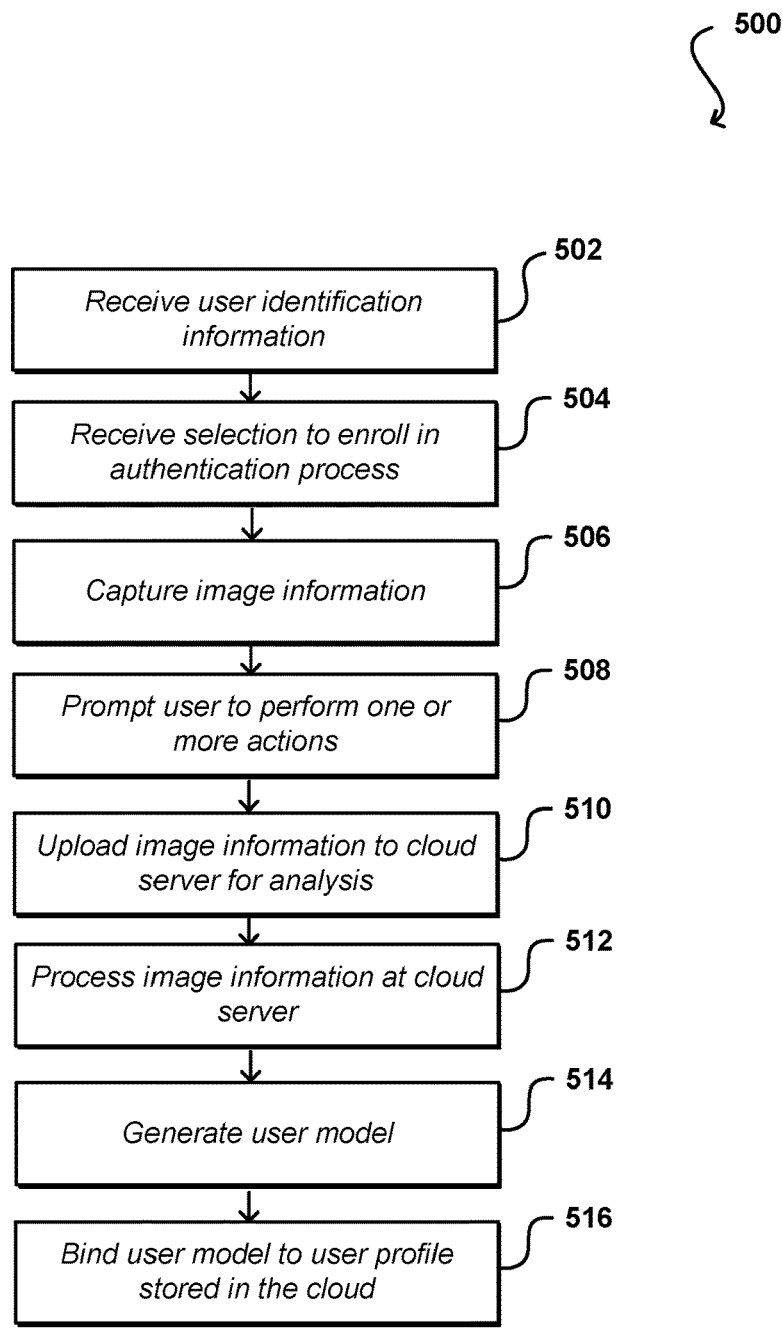
FIG. 5 illustrates an example process for configuring image-based authentication that can be utilized in accordance with various embodiments.

FIG. 5 illustrates an example process 500 for configuring a user authentication process that can be used in accordance with various embodiments. It should be understood that, for any process discussed herein, there can be additional, fewer, or alternative steps performed in similar or alternative orders, or in parallel, within the scope of the various embodiments unless otherwise stated. In this example, identifying information can be received 502 from a user to a device or application, such as by providing a username, password, identifier, or other such information. In at least some embodiments, the user might have previously provided such information as may be stored for the user, such as in a cookie or cache, to be used for a current session. In at least some embodiments, a selection can be received 504 from a user to enroll in the visual authentication process. In embodiments that are not tied to a particular application or device, a user might be able to provide information such as an email address and password, and use this information to authenticate the user's identity to any application or device that allows authentication using the visual authentication process. As mentioned, the process can trigger capture 506 of one or more images or video clips of the user for analysis. This can include, for example, three images captured at a time or a ten second video clip, for example. At or near a time of the capture, the process can prompt 508 the user to perform one or more actions, such as to perform a facial gesture, turn in a certain direction, etc. Once the image information is obtained, the image information can be uploaded 510 to another device, such as a cloud server, for analysis. The image information can be extracted, normalized, and otherwise processed 512 by an authentication module or other such component. A model for the user then can be generated 514 (or updated) by a cloud server or a related device having access to the processed image information. Any appropriate images, video clips, models, or other information then can be bound 516 to, and persisted with, the corresponding user profile. In at least some embodiments, the model can be automatically synchronized to multiple devices for the user, such as a mobile phone, a tablet computer, an e-book reader, and the like. The authentication information can be made available to various processes or devices as discussed elsewhere herein.

Figure 6:
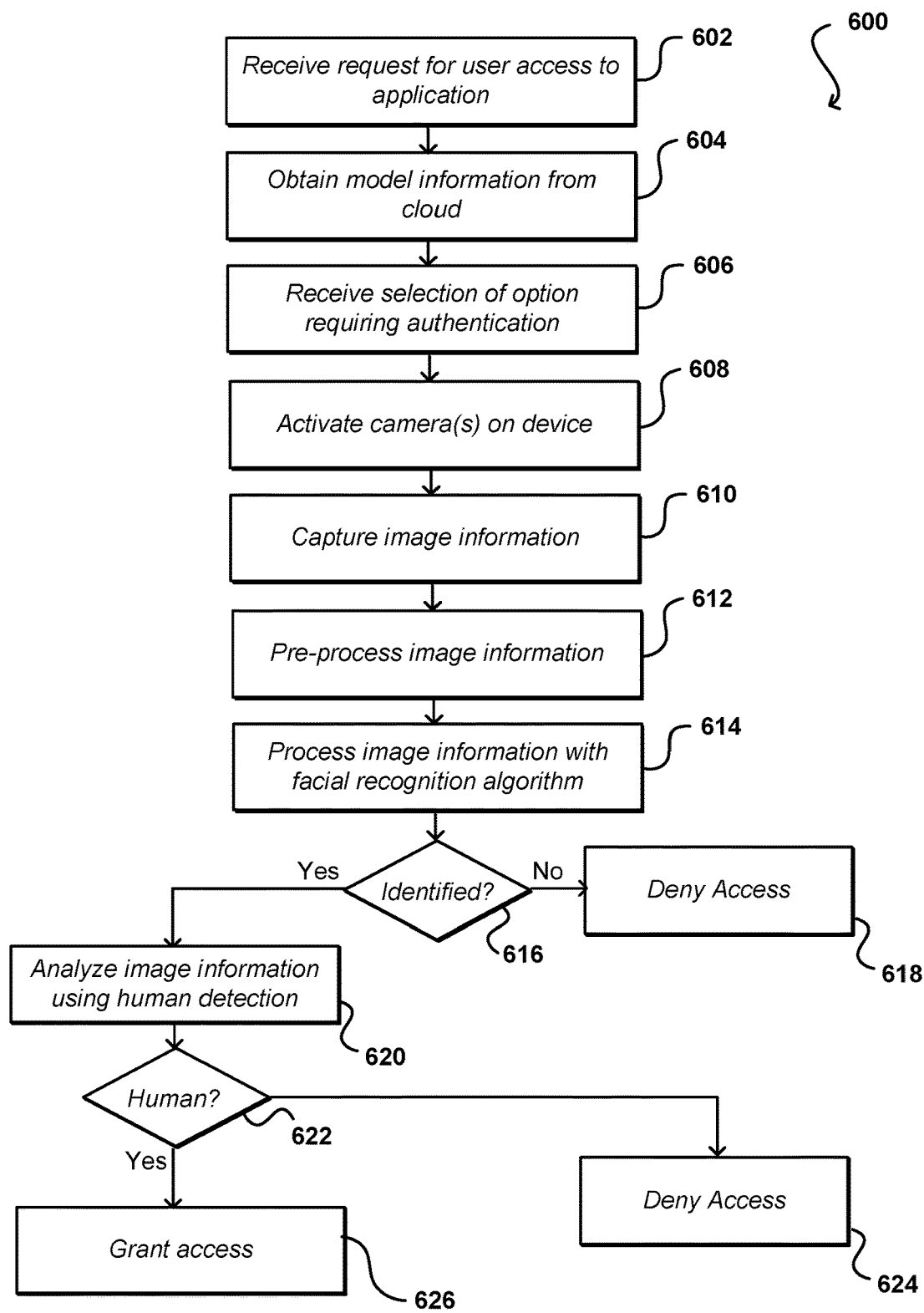
FIG. 6 illustrates an example process for utilizing image-based authentication in accordance with various embodiments.

FIG. 6 illustrates an example process 600 for authenticating a user using image information that can be utilized in accordance with various embodiments. In this example, a request is received 602 from a user to access an application or functionality on a computing device that is associated with a visual authentication process or other such approach as discussed elsewhere herein. In this example, an authentication module executing on the computing device can determine identify information about the user, such as upon the user entering username and/or password information, and can ensure that the latest visual model or other such information is obtained 604 from a location such as a cloud server or authentication service available across at least one network. As mentioned, visual and/or model information for a user profile can be stored in a network-accessible location for use by any of a number of different devices or applications for any of a number of authentication-related purposes.

At some point during the user session, a selection of an option can be received 606 from the user, where that option requires authentication of the user. As discussed elsewhere herein, this option can include a checkout at an e-commerce site, access to financial information, and the like. Depending at least in part upon configuration information, device capabilities, application requirements, or other such aspects, an image or video mode can be selected on the computing device for capturing image information for the authentication process. When an appropriate image capture mode is selected, one or more cameras can be activated 608 on the device and image information captured 610, such as may include a set of still images or a clip of video information. The captured image information in at least some embodiments can be pre-processed 612, such as by performing one or more filtering, cropping, or processing steps on the image information and, in the case of video information selecting one or more representative frames from the video, as may meet one or more selection criteria (e.g., head detected, relative orientation, etc.).

The image information can be processed to detect a location of a face in the image information, which can be marked in at least some embodiments. A face recognition algorithm can be used to process 614 the image information, to attempt to recognize the identity of the face in the image information with at least a minimum level of confidence. In one embodiment, a distance or score between 0 and 1 is determined between the face in the image information and the faces in the user information. Higher scores are associated with greater similarity between the faces. In certain algorithms, the distance of the image face and each registered user of the device is computed and the maximum score selected. If the selected face is similar enough to the user face information that the similarity value is higher than a pre-set similarity threshold, the customer can be identified

616. If the user is not identified, the user can be denied 618 access to functionality on the device. At the same time, before, or subsequent to the facial recognition process, a physical user determination can be made as well. In some embodiments, the physical user determination will be performed during the facial recognition process, which can take an amount of time to complete. In this example, the image information is analyzed 620 to determine whether the user captured in the image information is a physical user or a representation of a user. As discussed, this can involve capturing additional information with specific illumination activated, capturing video of a user performing a prompted action, etc. If the image information cannot be determined 622 to correspond to a live person with at least a minimum level of confidence, the user can be denied 624 access to functionality on the device. If the image information is determined to correspond to a live user, the user can be granted 626 access to the desired functionality. In some embodiments, a person who cannot be authenticated can be blocked from retrying the authentication process for at least a period of time in an attempt to minimize the ability to spoof the authentication process. Various other approaches can be utilized as well within the scope of the various embodiments.

In some embodiments, multiple human validation approaches can be used to attempt to verify that the image information actually includes information for a live person. A device can be configured to utilize multiple approaches by default, or can utilize additional approaches when one or more default approaches is unable to make a determination with at least a minimum level of confidence. In at least some embodiments, at least one environmental condition might affect the approach that is selected, such as may depend upon an amount of light or motion around the device, an amount of battery power of the device, and other such factors. When multiple approaches are used, a relative weight can be assigned to the result from each approach, and those results combined to attempt to come to a consensus as to whether the image information represents a physical person. The weighting can be determined using any appropriate criteria, such as past performance of an algorithm, current environmental conditions, or other such information.

In some embodiments other approaches can be used when image-based approaches alone cannot authenticate the user. A discussed, the user can be prompted to perform a certain action, say a certain word, or perform an action, although actions such as speaking a word can be spoofed as well. In some embodiments, the device can provide information that only the user would know, such as items the user has recently viewed or content the user has recently accessed, and can ask the user to select items meeting certain criteria (e.g., items the user purchased, articles the user read, etc.). Other approaches such as Captcha entry, question and answer entry, etc., can be used as well to attempt to authenticate the user. In certain embodiments, orders or actions that are allowed but where multiple approaches were needed to authenticate the user can be flagged for follow-up or other such action on behalf of a provider or other such entity.

In at least some embodiments, additional data points can be accumulated to improve the model of the user each time the user passes an authentication process. In some embodiments additional data might be accumulated when the confidence levels start dropping or various other criteria are met, in order to continually improve and/or refine the model. Such an approach can be particularly important for younger users whose facial features can changes significantly over a relatively short period of time.

In some embodiments, certain locations, IP addresses, or other information can be black listed or white listed as well. For example, if an IP address is associated with a user's home, that address might be added to a white list such that subsequent authentication is not necessary, or at least has to meet a lower standard. If an IP address is associated with fraudulent activity, that IP address might be black listed and not allowed to be used to authenticate a user. Various other such approaches can be used as well as known for addressing fraudulent activity.

Figure 7:
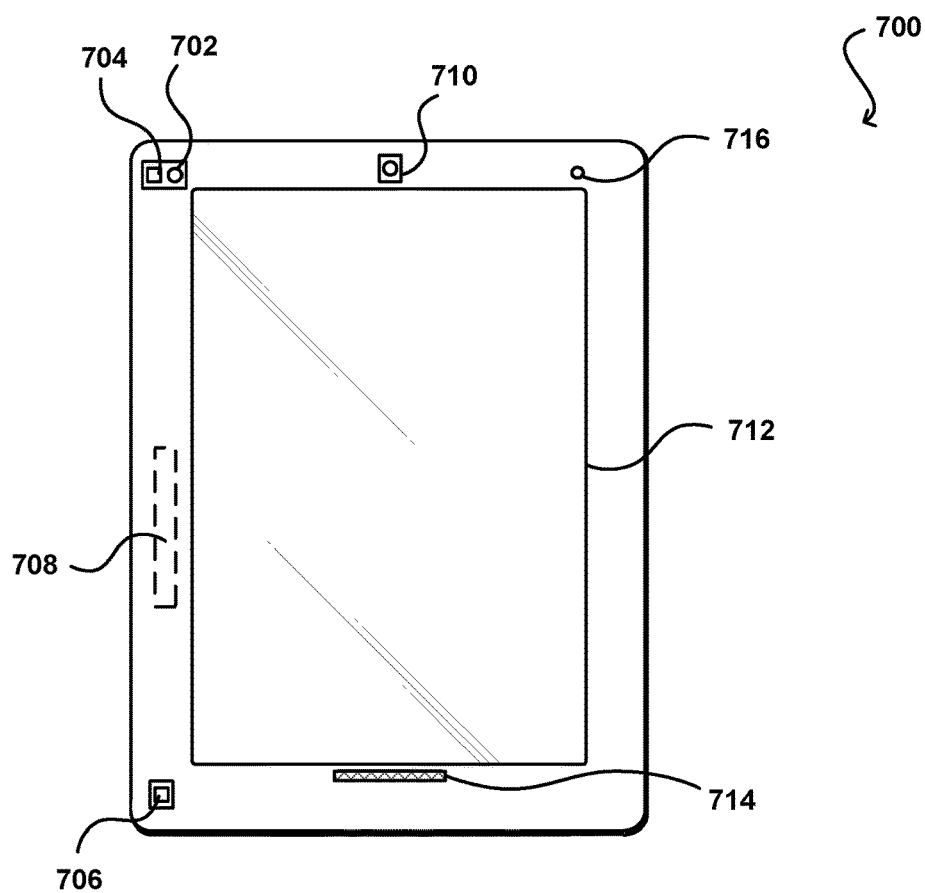
FIG. 7 illustrates an example computing device that can be utilized in accordance with various embodiments.

FIG. 7 illustrates an example of an electronic computing device 700 that can be used in accordance with various embodiments. As discussed, various other types of electronic devices can be used as well within the scope of the various embodiments. This example device includes a display element 712 for displaying information to a user as known in the art. The example device also includes at least one motion-determining element 708, such as an accelerometer or gyro element, which can be used to determine motion of the device, which can help to predict blur or focus of a captured image using various approaches described herein. The device also includes at least one image capture element for capturing image information about the user of the device. The imaging element may include, for example, a camera, a charge-coupled device (CCD), a motion detection sensor, or a radiation sensor, among many other possibilities. The example device in FIG. 7 includes a digital video camera 710 for capturing image information using ambient light as known in the art. The example device also includes an infrared (IR) emitter 702 and an IR detector 704. The device also includes another sensor that can be used for detecting IR or other radiation, or can be a lower resolution camera or other such components or discussed herein. The IR emitter 702 can be configured to emit IR radiation, and one or more of the detectors can detect the IR radiation reflected from a user (or other such surface or object).

The emitter(s) and detector(s), and any ambient light camera(s) or other image capture element(s), can be positioned on the device in locations that are least likely to interfere with the user's operation of the device. For example, if it is determined that average users hold the device by the middle of either side of the device and primarily on the right side or on the bottom of the device, then the emitter and detectors can be positioned at the corners of the device, primarily on the left-hand side or top of the device. In some embodiments, it might be useful for a user to participate in a calibration process which accounts for aspects such as the strength of eye reflection from the user, as well as to determine dimensions, calibrate direction determinations, etc. Such an approach also can be useful if a user uses glasses that reduce the reflective capability, etc.

The example device in FIG. 7 also includes a separate detection element 716, such as a motion sensor, heat signature detector, or light sensor. Such an element can provide input such as whether there is sufficient lighting for an image to be analyzed, as well as whether there is potentially a person in the room for purposes of activating an image capture or orientation-determining process. Further, a light-detecting sensor can help the device compensate for large adjustments in light or brightness, which can cause a user's pupils to dilate, etc. For example, when a user is operating a device in a dark room and someone turns on the light, the diameters of the user's pupils will change. As with the example above, if the device includes a display element that can operate in different modes, the device may also switch modes based on changes in the user's pupil dilation. In order for the device to not improperly interpret a change in separation between the device and user, the light detecting sensor might cause gaze tracking to be temporarily disabled until the user's eyes settle and a recalibration process is executed. Various other such approaches to compensate for light variations can be used as well within the scope of the various embodiments.

The example device 700 in FIG. 7 is shown to also include a microphone 714 or other such audio-capturing device. In some embodiments, the device can include multiple audio capture elements that can be used to help determine a relative direction or location of an audio source in two or three dimensions. The device in at least some embodiments can also trigger various actions based upon sound detected by the microphone. For example, if the device detects speech from a person, the device might activate video capture to attempt to locate and/or identify the person speaking.

In the example configuration of FIG. 7, each imaging element 704, 706, 716 is on the same general side of the computing device as a display element, such that when a user is viewing the interface in the display element the imaging element has a viewable area that, according to this example, includes the face of the user. While in some embodiments the imaging element is fixed relative to the device, in other embodiments the imaging element can be operable to track the position of the user, such as by rotating the imaging element or an optical element (e.g., a lens, mirror, etc.) that directs light to the imaging element. In some embodiments, the device can include capture elements on the sides, back, or corners of the device, or in any other such location, which can capture image information in any appropriate direction around the device. In some embodiments, a device can concurrently image and identify multiple persons in different locations around the device, and track those persons over time using the various elements.

Figure 8:
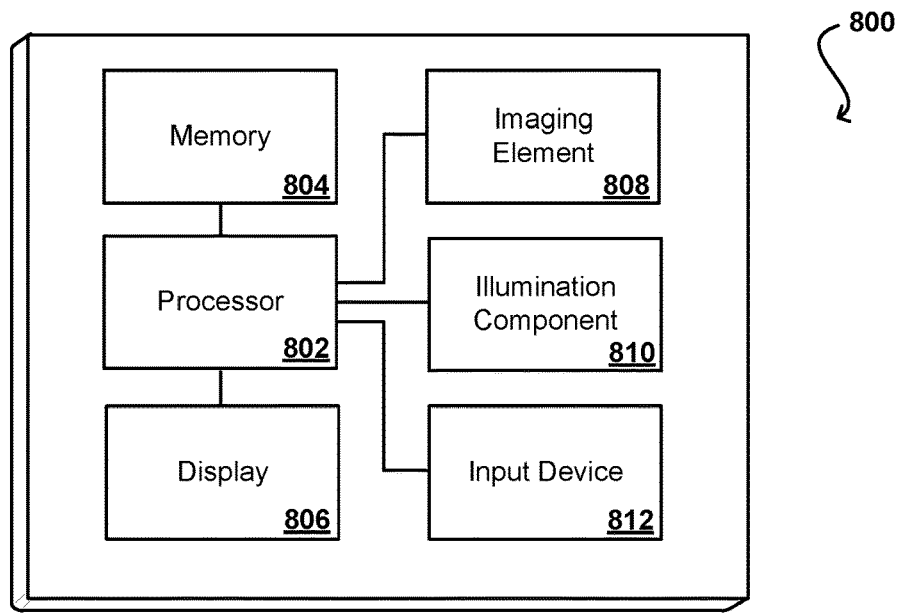
FIG. 8 illustrates example components of a device such as that illustrated in FIG. 7.

FIG. 8 illustrates a set of basic components of an example computing device 800 such as the devices described with respect to FIG. 7. While a portable smart device is depicted in many examples herein, the computing device could be any appropriate device able to receive and process input commands, such as a personal computer, laptop computer, television set top box, cellular phone, PDA, electronic book reading device, video game system, or portable media player, among others. In this example, the device includes a processor 802 for executing instructions that can be stored in a memory device or element 804. As known in the art, the device can include many types of memory, data storage or computer-readable media, such as a first data storage for program instructions for execution by the processor 802, a separate storage for images or data, a removable memory for sharing information with other devices, etc. The device typically will include some type of display element 806, such as a liquid crystal display (LCD), although devices such as portable media players might convey information via other means, such as through audio speakers. As discussed, the device in many embodiments will include at least one imaging element 808 such as a camera, sensor, or detector that is able to image a facial region of a user. The imaging element can include any appropriate technology, such as a CCD imaging element having a sufficient resolution, focal range and viewable area to capture an image of the user when the user is operating the device. Methods for capturing images using an imaging element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application or other device.

In some embodiments, the device can include at least illumination component 810 that is able to assist in image capture by emitting light over a desired range or with a desired pattern. The component can include one or more light emitting diodes (LEDs) or other such elements, operable to emit light over visible and/or IR spectrum, for example. The device can include at least one additional input device 812 able to receive conventional input from a user. This conventional input can include, for example, a push button, touch pad, touch-sensitive element used with a display, wheel, joystick, keyboard, mouse, keypad or any other such device or element whereby a user can input a command to the device. Some devices also can include a microphone or other audio capture element that accepts voice or other audio commands. For example, a device might not include any buttons at all, but might be controlled only through a combination of visual and audio commands, such that a user can control the device without having to be in contact with the device. As will be discussed later herein, functionality of these additional input devices can also be adjusted or controlled based at least in part upon the determined gaze direction of a user or other such information.

In some embodiments, one or more icons or other notifications might be displayed on the device to indicate to the user that IR illumination is active, or that image recognition is being performed. In some embodiments, a light (e.g., LED) on the device might illuminate in order to notify the user that facial recognition is activated in order to signal to the user that the user should look at the device and remain relatively still until the process can complete. Various other notifications can be used as well as appropriate.

As will be appreciated, although a Web-based environment is used for purposes of explanation in many examples, different environments may be used, as appropriate, to implement various embodiments. An environment can include a variety of electronic client devices, which can include any appropriate device operable to send and receive requests, messages, or information over an appropriate network and convey information back to a user of the device. Examples of such client devices include personal computers, cell phones, handheld messaging devices, laptop computers, set-top boxes, personal data assistants, electronic book readers, and the like. Each client device can be capable of running at least one motion or orientation-controlled interface as discussed or suggested herein. In some cases, all the functionality for the interface will be generated on the device. In other embodiments, at least some of the functionality or content will be generated in response to instructions or information received from over at least one network.

The network can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections, and combinations thereof.

Each content provider can include at least one application server or other such server in communication with at least one data store. It should be understood that there can be several application servers, layers, and/or other elements, processes, or components, which may be chained or otherwise configured, which can interact to perform tasks such as obtaining data from an appropriate data store. As used herein the term "data store" refers to any device or combination of devices capable of storing, accessing, and retrieving data, which may include any combination and number of data servers, databases, data storage devices, and data storage media, in any standard, distributed, or clustered environment. An application server can include any appropriate hardware and software for integrating with the data store as needed to execute aspects of one or more applications for the client device, handling a majority of the data access and business logic for an application. The application server provides access control services in cooperation with the data store, and is able to generate content such as text, graphics, audio, and/or video to be transferred to the user, which may be served to the user by the Web server in the form of HTML, XML, or another appropriate structured language in this example. The handling of all requests and responses, as well as the delivery of content between the client device and an application server, can be handled by the respective Web server. It should be understood that the Web and application servers are not required and are merely example components, as structured code discussed herein can be executed on any appropriate device or host machine as discussed elsewhere herein. Further, the environment can be architected in such a way that a test automation framework can be provided as a service to which a user or application can subscribe. A test automation framework can be provided as an implementation of any of the various testing patterns discussed herein, although various other implementations can be used as well, as discussed or suggested herein.

Each data store can include several separate data tables, databases, or other data storage mechanisms and media for storing data relating to a particular aspect. It should be understood that there can be many aspects that may need to be stored in a data store, such as access right information, which can be stored in any of the above listed mechanisms as appropriate or in additional mechanisms in the data store. Each data store is operable, through logic associated therewith, to receive instructions from a respective application server and obtain, update, or otherwise process data in response thereto. In one example, a user might submit a search request for a certain type of content. In this case, the data store might access the user information to verify the identity of the user, and can access the content information to obtain information about instances of that type of content. The information then can be returned to the user, such as in a results listing on a Web page that the user is able to view via a browser on the user device. Information for a particular instance of content can be viewed in a dedicated page or window of the browser.

Each server typically will include an operating system that provides executable program instructions for the general administration and operation of that server, and typically will include a computer-readable medium storing instructions that, when executed by a processor of the server, allow the server to perform its intended functions. Suitable implementations for the operating system and general functionality of the servers are known or commercially available, and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated or discussed herein. Thus, the depiction of various systems should be taken as being illustrative in nature, and not limiting to the scope of the disclosure.

Various embodiments discussed or suggested herein can be implemented in a wide variety of operating environments, which in some cases can include one or more user computers, computing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A mobile device, comprising:
a processor; and
memory storing instructions that, as a result of being executed by the processor, cause the mobile device to:
obtain a request to authorize a transaction;
illuminate, with an infrared light emitting diode, a user that is interacting with the mobile device;
use a camera on the mobile device to capture an infrared image of a portion of a face of the user;
analyze the infrared image to identify eyes of the user;
determine that the infrared image corresponds to a living being by analyzing a thermal characteristic of the eyes of the user;
identify the user based at least in part on the infrared image;
authenticate the user as a result of the identity of the user being recognized as an authorized user and as a result of the infrared image corresponding to a living being; and
allow the transaction to be performed as a result of the user being authenticated.

2. The mobile device of claim 1, wherein the infrared image captures a reflection of infrared light emitted from the infrared light emitting diode.

3. The mobile device of claim 1, wherein the instructions further cause the mobile device to:
obtain identifying information for an authorized user by performing a visual authentication enrollment process; and
authenticate the user as a result of the identity of the user being recognized as the authorized user associated with the identifying information.

4. The mobile device of claim 1, wherein the infrared light emitting diode is on the mobile device.

5. The mobile device of claim 1, wherein:
the camera is capable of capturing thermal information; and
the infrared image includes thermal imaging data.

6. A computer-implemented method of authenticating a user of a mobile device, comprising:
projecting an infrared light onto a user that is interacting with the mobile device;
capturing an infrared image of a portion of the user with a camera on the mobile device;
analyzing the infrared image to identify an eye of the user;
determining that the infrared image corresponds to a living being by analyzing a variance in a thermal characteristic of the eye;
identifying the user based at least in part on the infrared image; and
authenticating the user as a result of the identity of the user being recognized as an authorized user and as a result of the infrared image corresponding to a living being.

7. The computer-implemented method of claim 6, wherein:
facial data of the user is collected as part of a visual authentication enrollment process;
facial data of the user is obtained from the infrared image using a facial recognition algorithm; and
the identity of the user is determined based at least in part on the facial data.

8. The computer-implemented method of claim 6, further comprising directing the user to look at the camera on the mobile device.

9. The computer-implemented method of claim 6, wherein the infrared light is projected using an infrared light emitting diode under the control of the mobile device.

10. The computer-implemented method of claim 6, further comprising obtaining the infrared image from a sequence of images in a video stream.

11. The computer-implemented method of claim 6, further comprising:
obtaining a second image of the user, the second image representing light captured from a visible spectrum; and
identifying the user based at least in part on the second image.

12. The computer-implemented method of claim 6, further comprising:
detecting that the user is looking at the camera; and initiating an authentication process as a result of detecting that the user is looking at the camera.

13. The computer-implemented method of claim 6, further comprising:
   capturing a sequence of images of the eye of the user;
   detecting a blink of the eye based on the sequence of images; and
   determining that the image represents a living being as a result of detecting the blink.

14. The computer-implemented method of claim 6, further comprising presenting a signal to the user indicating that the user should look at the mobile device to perform an authentication process.

15. The computer-implemented method of claim 6, further comprising:
   obtaining a request to authorize a transaction; and
   determining that the identified user is authorized to perform the transaction.

16. The computer-implemented method of claim 15, further comprising denying the transaction as a result of determining that the image does not correspond to a physical being.

17. A non-transitory computer-readable storage medium storing instructions that, as a result of being executed by a processor on a mobile computing device, cause the mobile computing device to:
   project an infrared light onto a user that is interacting with the mobile computing device;
   capture an infrared image of a portion of the user with a camera on the mobile computing device;
   analyze the infrared image to identify an eye of the user;
   determine that the infrared image corresponds to a living being by analyzing a variance in a thermal characteristic of the eye;
   identify the user based at least in part on the infrared image; and
   authorize a request initiated by the user as a result of the user being recognized as an authorized user stored in memory on the mobile computing device and as a result of the image corresponding to a physical being.

18. The non-transitory computer-readable storage medium of claim 17, wherein the instructions executable to further cause the mobile computing device to:
   as part of a visual authentication enrolment process, project an infrared light on to a face of an authorized user;
   capture a reflection of the infrared light from the eye of the user using the camera; and
   store a characteristic of the eye.

19. The non-transitory computer-readable storage medium of claim 17, wherein the instructions executable to further cause the mobile computing device to determine that the gaze of the user is directed at the device.

20. The non-transitory computer-readable storage medium of claim 17, wherein the instructions executable to further cause the mobile computing device to:
   obtain a request to authorize a transaction; and
   deny the transaction as a result of determining that the image does not correspond to a physical being.

* * * * *